(12) United States Patent
Kim

(10) Patent No.: US 8,226,410 B2
(45) Date of Patent: Jul. 24, 2012

(54) MOUNT DEVICE FOR DENTAL IMPLANT

(76) Inventor: Jeong Chan Kim, Seoul (KR)

( * ) Notice: Subject to any disclaimer, the term of this patent is extended or adjusted under 35 U.S.C. 154(b) by 709 days.

(21) Appl. No.: 11/721,270

(22) PCT Filed: Feb. 3, 2006

(86) PCT No.: PCT/KR2006/000396
§ 371 (c)(1),
(2), (4) Date: Jul. 9, 2009

(87) PCT Pub. No.: WO2006/088291
PCT Pub. Date: Aug. 24, 2006

(65) Prior Publication Data
US 2009/0291413 A1    Nov. 26, 2009

(30) Foreign Application Priority Data

Feb. 15, 2005    (KR) ........................ 10-2005-0012210

(51) Int. Cl.
*A61C 8/00*    (2006.01)
(52) U.S. Cl. ........................................ 433/174
(58) Field of Classification Search .......... 433/172–175, 433/199.1, 200.1, 201.1, 204, 206, 211, 141, 433/225; 81/436, 447, 459; 606/300–321
See application file for complete search history.

(56) References Cited

U.S. PATENT DOCUMENTS 4,995,810 A * 2/1991 Soderberg ..................... 433/141
6,083,004 A    7/2000 Mish et al.

FOREIGN PATENT DOCUMENTS

| WO | WO9917676 | 4/1999 |
|---|---|---|
| WO | WO03030767 | 4/2003 |

OTHER PUBLICATIONS

International Search Report; PCT/KR2006/000396; May 26, 2006.
Written Opinion of the International Searching Authority; PCT/KR2006/000396; May 26, 2006 All the references cited in the Search Report and the Written Opinion are listed above.

* cited by examiner

*Primary Examiner* — Cris L Rodriguez
*Assistant Examiner* — Mirayda A Aponte
(74) *Attorney, Agent, or Firm* — Cantor Colburn LLP

(57) ABSTRACT

A mount device for a dental implant to place a fixture having an inner hole in an alveolar bone includes a mount screw having a body portion with a first screw portion and a second screw portion, and a head portion having a sectional area larger than that of the body portion, coupled to an upper end portion of the body portion, and detachably coupled to a handpiece through a handpiece connector, and a mount having an inclined surface formed on either an inner wall or an outer wall of the lower end portion for a conical connection to the upper end portion of the fixture, an insertion hole formed inside the mount along a lengthwise direction, and a second inner screw portion formed on an inner wall of the insertion hole and capable of screw coupling to the second screw portion. To remove a screw coupling between the second inner screw portion and the second screw portion when an upper end surface of the mount contacts a lower end surface of the head portion, a distance from a lower end of the second inner screw portion to the upper end of the mount is less than a distance from an upper end of the second screw portion to a lower end of the head portion.

6 Claims, 11 Drawing Sheets

MOUNT DEVICE FOR DENTAL IMPLANT

BACKGROUND OF THE INVENTION

1. Field of the Invention

The present invention relates to a mount device for dental implant, and more particularly, to a mount device for dental implant used to place a fixture in an alveolar bone.

2. Description of the Related Art

Originally, implant means a replacement to restore human tissues when the human tissues are lost. In the dentistry, the implant means transplantation of an artificial tooth root. The dental implant is a state-of-the-art treatment which helps the restoration of a function of a tooth by placing a tooth root made of titanium that does not show organ rejection in a bone where a tooth is missing and fixing an artificial tooth thereon, to replace the root of the missing tooth. For a general prosthesis or denture, neighboring teeth and bone are damaged as time passes. However, the dental implant does not damage neighboring tooth tissues and provides the same function or shape of a natural tooth without generating a decayed tooth, so that it can be used semi-permanently.

The dental implant treatment is a revolutionary development that is compared to the Industrial Revolution in the field of dentistry. Due to this development, a variety of implants are introduced into the market so that scores of implants including domestic and foreign implants exist in the market. Since the various types of implants have different structures and shapes, many dentists are confused and have difficulty in treatment. Such difficulty sometimes makes an implant treatment a failure.

Thus, making the implant treatment easier and reducing a treatment time are necessary jobs to achieve for both of a dentist and a patient. In the implant treatment, not only a step of easily placing an implant but also a step of easily removing a mount device that enables placing of the implant is important.

In the structure of a dental implant, as shown in FIG. 1, a fixture 150 that is an artificial tooth root is first placed in upper and lower jawbones 180 (hereinafter, referred to as the alveolar bone) like a root of a natural tooth. The fixture 150 is osseointegrated to be completely fixed to the alveolar bone 180. After the osseointegration, an abutment 190 is connected to the fixture 150 of the dental implant using an abutment screw (not shown) and an artificial crown 170 is mounted thereon, so that an implant artificial tooth is completed. The fixture 150 of the dental implant passes through a compact bone having a relatively higher bone density and placed in a spongy bone 180b having a relatively lower bone density.

When the fixture of a dental implant is placed in the alveolar bone, a mount is coupled to the fixture using a mount screw. An upper end portion of the mount screw is inserted in a handpiece through a handpiece connector and rotated by a strong rotational force so that the fixture is placed in the alveolar bone.

However, a coupling hole formed in the alveolar bone in advance for the placement of the fixture has a diameter smaller than the outer diameter of a screw formed on the fixture. Also, since the fixture is placed in the alveolar bone while making a screw therein. Thus, for a fixture in which the fixture and the mount are coupled in a conical connection, a strong torque is generated between the inner surface of the fixture and the outer surface of the mount during the placement of the fixture so that the fixture and the mount closely contact each other.

When there is no special structure to remove a state in which the inner surface of the fixture 150 and the outer surface of the mount closely contact each other by the strong torque applied therebetween after the fixture is placed, if the handpiece is rotated in the reverse direction for the placement to separate the mount device from the fixture, not only the mount device but also the fixture is pulled out.

Thus, a structure to prevent the above phenomenon is needed. Although a variety of structures to disassemble the mount device only after the placement of the fixture have been suggested, it is a problem that the structure is complicated in most cases.

To consider the problem, a mount device 101 for a dental implant having a structure as shown in FIGS. 2 through 5 has been introduced. The mount device 101 includes a mount screw 110 including a body portion 111 having a first screw portion 112 where a right screw is formed at a lower end portion thereof and a second screw portion 113 where a left screw is formed at a position separated a predetermined distance upward from the first screw portion 112, and a mount 120 provided on an inner side wall of an insertion hole 122 where a second inner screw portion 123 that can be screw coupled to the second screw portion 113 of the mount screw 110 is formed by penetrating the same.

In the structure, when the fixture 150 is placed, the second inner screw portion 123 of the mount 120 is coupled to the second screw portion 113 of the mount screw 110 and the first screw portion 112 of the mount screw 110 is coupled to a first inner screw portion 152 of an inner hole 153 of the fixture 150. When the mount screw 110 is rotated clockwise as shown in FIG. 2 using a handpiece 160 which connects the mount screw 110 via a handpiece connector 140, the mount screw 110 does not relatively rotate against the fixture 150 and is rotated together with the fixture 150.

This is because, in addition to the screw coupling between the first screw portion 112 of the mount screw 110 and the first inner screw portion 152 of the fixture 150, when the mount screw 110 is rotated clockwise using the handpiece, since the second screw portion 113 of the mount screw 110 is a left screw, the mount 120 is moved in a direction such that the second screw portion 113 of the mount screw 110 is separated from the second inner screw portion 123 of the mount 120. As a result, as shown in FIG. 2, an inclined surface 121 of the mount 120 and a fixture inner inclined surface 151 closely contact each other so that a friction force is applied therebetween.

That is, in addition to the screw coupling between the first screw portion 112 of the mount screw 110 and the first inner screw portion 152 of the fixture 150, the frictional force between the inclined surface 121 of the mount 120 and the fixture inner inclined surface 151, where a contact area is large, acts as a main force to rotate the fixture 150, thus rotating the fixture 150 together with the mount screw 110. As the fixture 150 is placed in the alveolar bone 180 to a predetermined depth while rotates, the placement is completed.

Next, in order to remove the mount device 101 after the fixture 150 is placed, a mount holder 130 is coupled to the mount 120 as shown in FIG. 3. The mount screw 110 is rotated counterclockwise in the opposite direction for the placement while either the mount hole 130 prevents the mount 120 from rotating or the mount holder 130 rotates the mount 120 clockwise, Then, the mount 120 is move upward as shown in FIG. 4 such that the second screw portion 113 of the mount screw 110 and the second inner screw portion 123 of the mount 120 are screw coupled to each other. Accordingly, the state of the inclined surface 121 of the mount 120 pressed against the fixture inner inclined surface 151 is removed so that the frictional force is no longer applied therebetween. Thus, only the mount screw 110 relatively rotates with respect to the fixture 150 placed in the alveolar bone and is disassembled from the fixture 150.

The reason for fixing the mount 120 using the mount holder 130 will be described in detail for a better understanding. Assuming that the mount screw 110 is rotate counterclockwise without fixing the mount 120 using the mount holder 130, since the inclined surface 121 of the mount 120 and the fixture inner inclined surface 151 closely contact each other after the replacement, the force rotating the mount screw 110 counterclockwise makes the frictional force between the inclined surface 121 of the mount 120 and the fixture inner inclined surface 151 act in a direction to rotate the fixture 150 counterclockwise and the mount 120 clockwise.

As mentioned above, since the frictional force is a main force to rotate the fixture 150, the frictional force acting in a direction to rotate the fixture 150 counterclockwise means that the mount screw 110 and the fixture 150 rotate together so that the fixture 150 finally comes out as well.

However, when the mount screw 110 is rotated counterclockwise while fixing the mount 120 using the mount holder 130 or rotating the mount 120 clockwise, the force rotating the mount screw 110 counterclockwise makes the frictional force between the inclined surface 121 of the mount 120 and the fixture inner inclined surface 151 act in a direction to support the counterclockwise rotation of the fixture 150, that is, clockwise, and in a direction to rotate the mount 120 counterclockwise. The frictional force acting in a direction to rotate the fixture 150 counterclockwise means that the rotation of the fixture 150 with the mount screw 110 is obstructed by the frictional force and the fixture 150 maintains a placed state without being rotated counterclockwise.

In the meantime, in the conventional mount device for a dental implant, since the second screw portion 113 of the mount screw 110 is formed so closely to a head portion 115, when the fixture is placed in the alveolar bone and the mount device 101 is removed, if the handpiece 160 is rotated counterclockwise while fixing the mount 120 using the mount holder 130 or rotating the mount 120 clockwise using the mount holder 130, the mount 120 is moved upward toward the mount screw 110 by the rotation of the mount screw 110. Then, before the screw coupling between the second screw portion 113 of the mount screw 110 and the second inner screw portion 123 of the mount 120 is removed, the lower end surface of the head portion 115 of the mount screw 110 and the upper end portion of the mount 120 closely contact each other as shown in FIG. 5 so that the handpiece 160 connected to the mount holder 130 cannot be rotated any longer. Thus, it is a problem that, only when the rotation of the handpiece 160 is stopped and the mount holder 130 is removed from the mount 120, the mount device 101 can be removed by continuously rotating the handpiece 160 counterclockwise.

Hence, an implant operation is made very inconvenient and the inconvenient operation is performed inside a mount of a patient which is very narrow and difficult to view so that the pain of patients undergoing operations increases and dentists are also inconvenienced. In particular, since the mount holder 130 is used inside the mount of a patent, it is difficult to make the mount holder 130 thick. Thus, when an open ended wrench having an insufficient thickness is used as the mount holder 130, the open portion is easily widened, which makes the use of the open ended wrench inappropriate. Alternatively, when a slugging ring wrench is used, since the handpiece connector 140 and the handpiece 160 need to be completely separated from each other to detach the mount holder 130, the implant operation is made very inconvenient, the operation time remarkably extends, and the dentists are inconvenienced.

As shown in FIGS. 2 through 5, according to the conventional technology, since the mount 120 is conical such that the outer diameter of the lower end portion is less than that of the upper end portion, and the lower end portion of the mount 120 is inserted in the fixture 150, the upper end portion of the fixture 150 has a thin thickness. When the mount 120 is inserted in the fixture 150 and contacts the same, since the mount 120 applies a force in a radial direction of the fixture 150, the upper end portion of the fixture 150 is frequently damaged.

BRIEF SUMMARY OF THE INVENTION

To solve the above and/or other problems, the present invention provides a mount device for a dental implant which has a simple structure and can remove the mount device without disassembling the mount holder from the mount so that an implant operation is made very easy and the operation time can be greatly reduced, compared to the conventional technology, while solving the inconvenience in the operation according to the conventional technology in which the mount device can be removed by stopping the rotation of the handpiece at a certain time point and removing the mount holder from the mount and then continuously rotating the handpiece counterclockwise while rotating the handpiece connected to the mount screw through the handpiece connector counterclockwise with the mount holder fixed to the mount to remove the mount device after the fixture is placed in the alveolar bone.

Also, the present invention provides a mount device for a dental implant which can reduced the possibility of the upper end portion of the fixture being damaged.

According to an aspect of the present invention, a mount device for a dental implant to place a fixture in an alveolar bone, the fixture having an inner hole formed inside to have a predetermined depth along a lengthwise direction from an upper end of the fixture to a lower end thereof, comprises a mount screw including a body portion having a first screw portion provided at the lower end of the body portion to be capable of screw coupling to a first inner screw portion of the fixture and a second screw portion having a screw formed in a direction opposite to a direction of a screw of the first screw portion and provided at a position separated a predetermined distance upward from the first screw portion, and a head portion having a sectional area larger than that of the body portion, coupled to an upper end portion of the body portion, and detachably coupled to a handpiece for a dental use through a handpiece connector, and a mount having an inclined surface formed on at least one of an inner wall and an outer wall of the lower end portion for a conical connection to the upper end portion of the fixture, an insertion hole formed inside the mount along a lengthwise direction from the upper end to a lower end thereof by penetrating the mount, and a second inner screw portion formed on an inner wall of the insertion hole and capable of screw coupling to the second screw portion, in which, to remove a screw coupling between the second inner screw portion of the mount and the second screw portion of the mount screw when an upper end surface of the mount contacts a lower end surface of the head portion of the mount screw, a distance from a lower end of the second inner screw portion of the mount to the upper end of the mount is less than a distance from an upper end of the second screw portion of the mount screw to a lower end of the head portion.

A lower end portion of the mount has an outer diameter which decreases toward a lower end thereof so that the inclined surface is formed on an outer wall of the lower end portion of the mount, and the inclined surface has a conical connection to a fixture inner inclined surface formed on the inner wall of the fixture.

A lower end portion of the mount has an inner diameter which increases toward a lower end thereof so that the inclined surface is formed on an inner wall of the lower end portion of the mount, and the inclined surface has a conical connection to a fixture outer inclined surface formed on the outer wall of the fixture. Thus, a possibility of the upper end portion of the fixture being damaged can be reduced compared to the conventional technology.

The first screw portion is a right screw and the second screw portion is a left screw.

A distance from a lower end of the second inner screw portion of the mount to the upper end of the mount is 0.01-3 mm shorter than a distance from an upper end of the second screw portion of the mount screw to a lower end of the head portion.

According to the present invention, the mount device for a dental implant has a simple structure and can remove the mount device without disassembling the mount holder from the mount so that an implant operation is made very easy and the operation time can be greatly reduced, compared to the conventional technology, while solving the inconvenience in the operation according to the conventional technology in which the mount device can be removed by stopping the rotation of the handpiece at a certain time point and removing the mount holder from the mount and then continuously rotating the handpiece counterclockwise while rotating the handpiece connected to the mount screw through the handpiece connector counterclockwise with the mount holder fixed to the mount to remove the mount device after the fixture is placed in the alveolar bone.

Accordingly, the implant operation is made easy and the operation time is greatly reduced, compared to the conventional technology, so that the pain of patients undergoing operations is alleviated and convenience is provided to dentists, thus increasing the possibility of success of an operation.

Furthermore, since the lower end portion of the mount has an inner diameter that increases toward the lower end thereof such that the inclined surface of the mount is formed on the inner wall of the lower end portion of the mount, and the inclined surface of the mount has a conical connection to the outer inclined surface of the fixture formed on the outer wall of the fixture, the possibility of the upper end portion of the fixture being damaged is further reduced compared to the conventional technology.

DETAILED DESCRIPTION OF THE INVENTION

Figure 1:
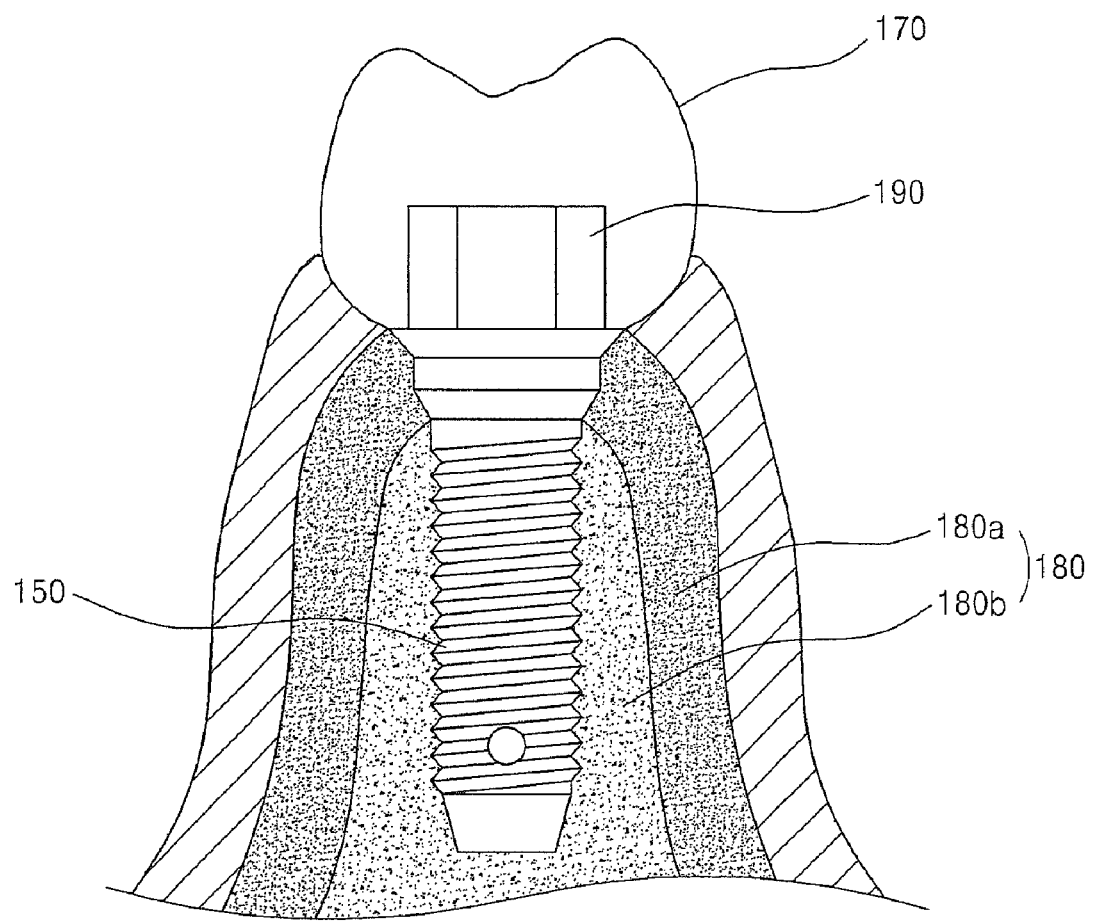
FIG. 1 is a view illustrating the configuration of a general dental implant.
Figure 2:
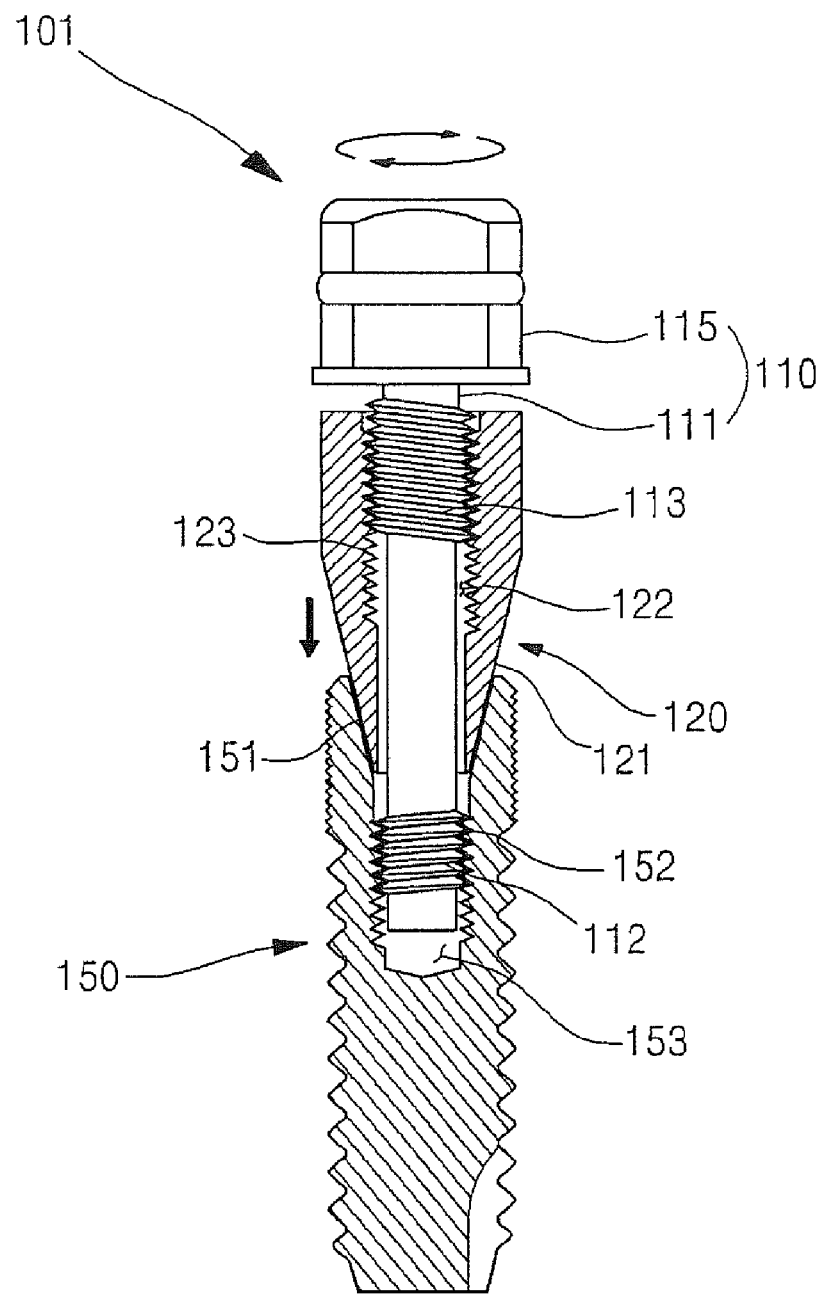
FIG. 2 is a sectional view illustrating a state in which a fixture is placed using a conventional mount device for a dental implant.
Figure 3:
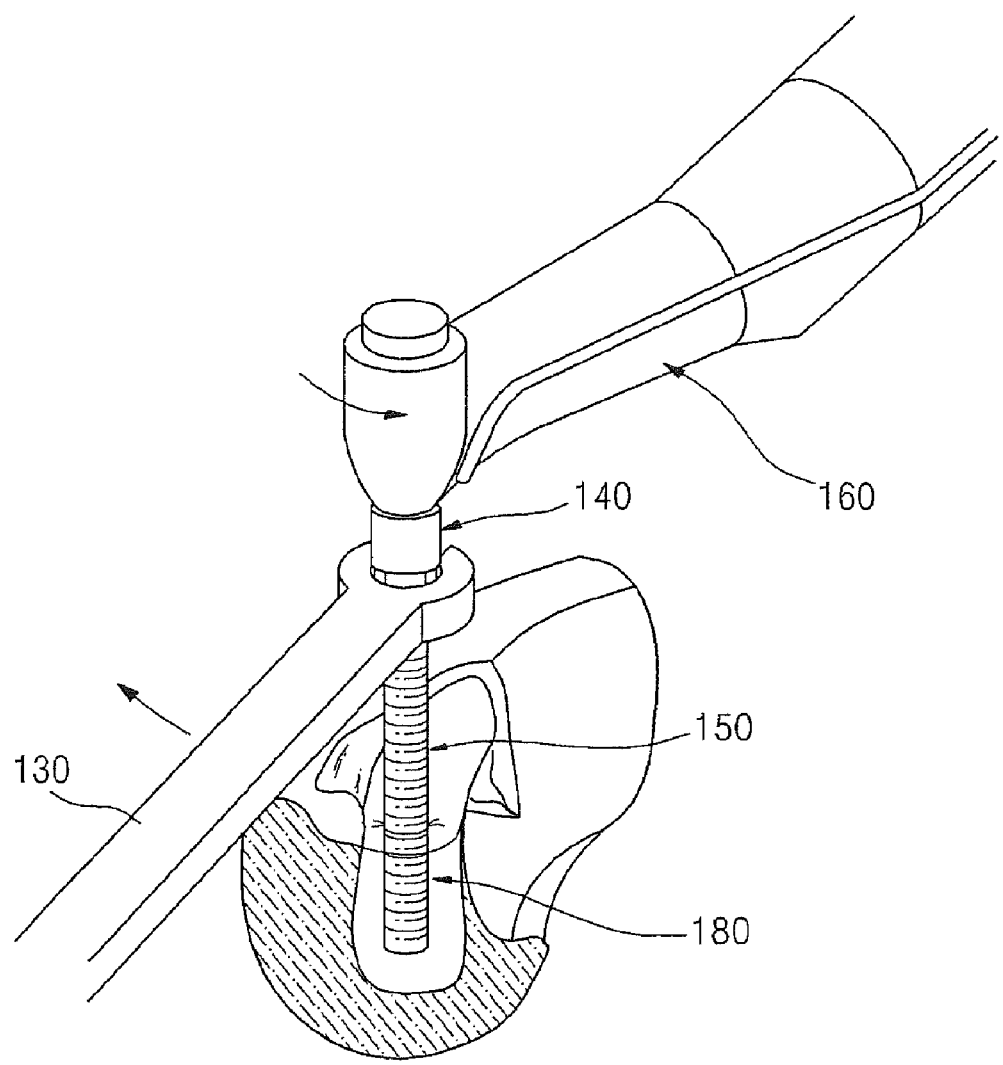
FIG. 3 is a perspective view illustrating a state in which a mount holder is coupled to a mount to separate the mount device for a dental implant of FIG. 2 after the fixture is placed.
Figure 4:
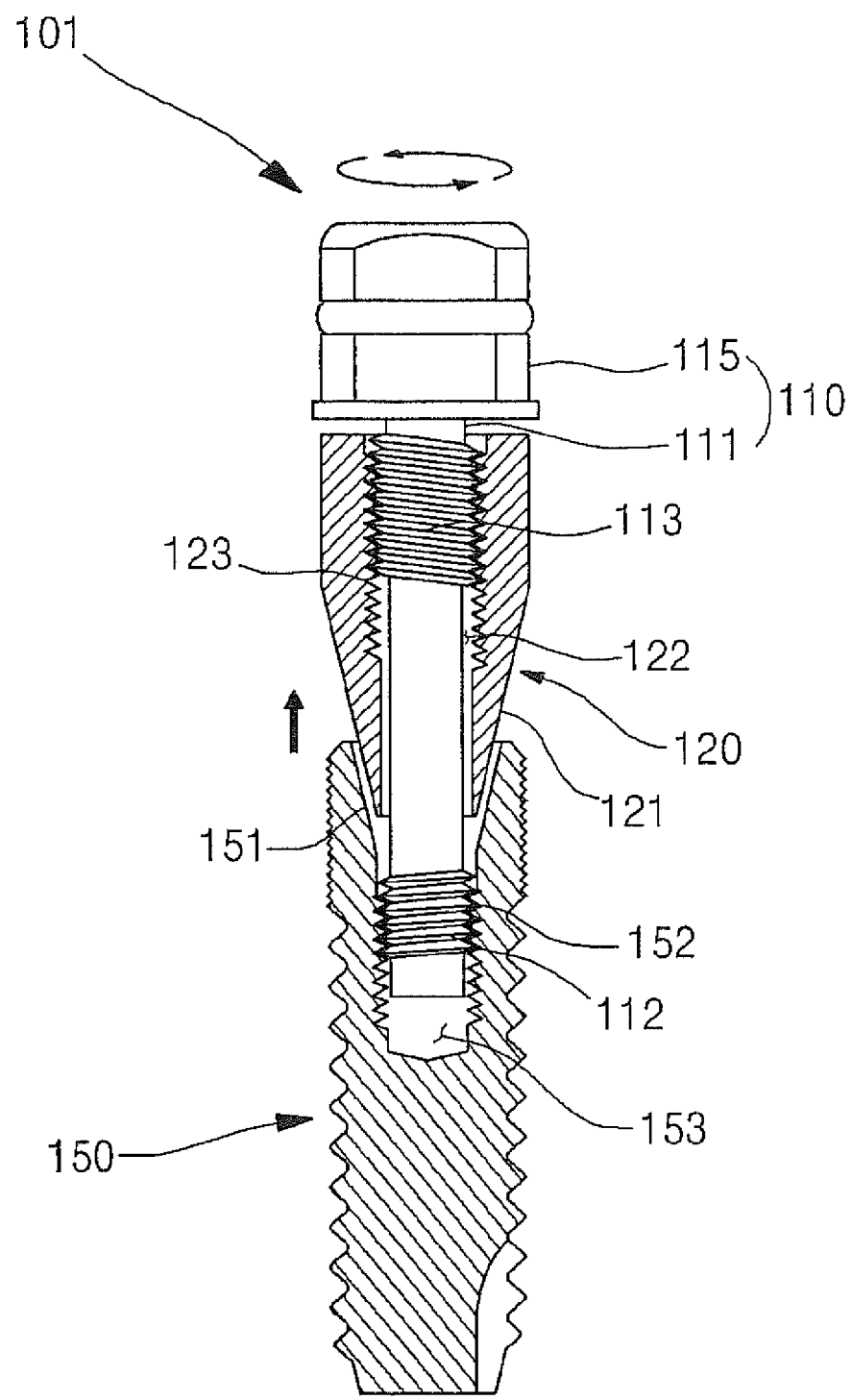
FIG. 4 is a view for explaining a process of separating the mount device for a dental implant of FIG. 3.
Figure 5:
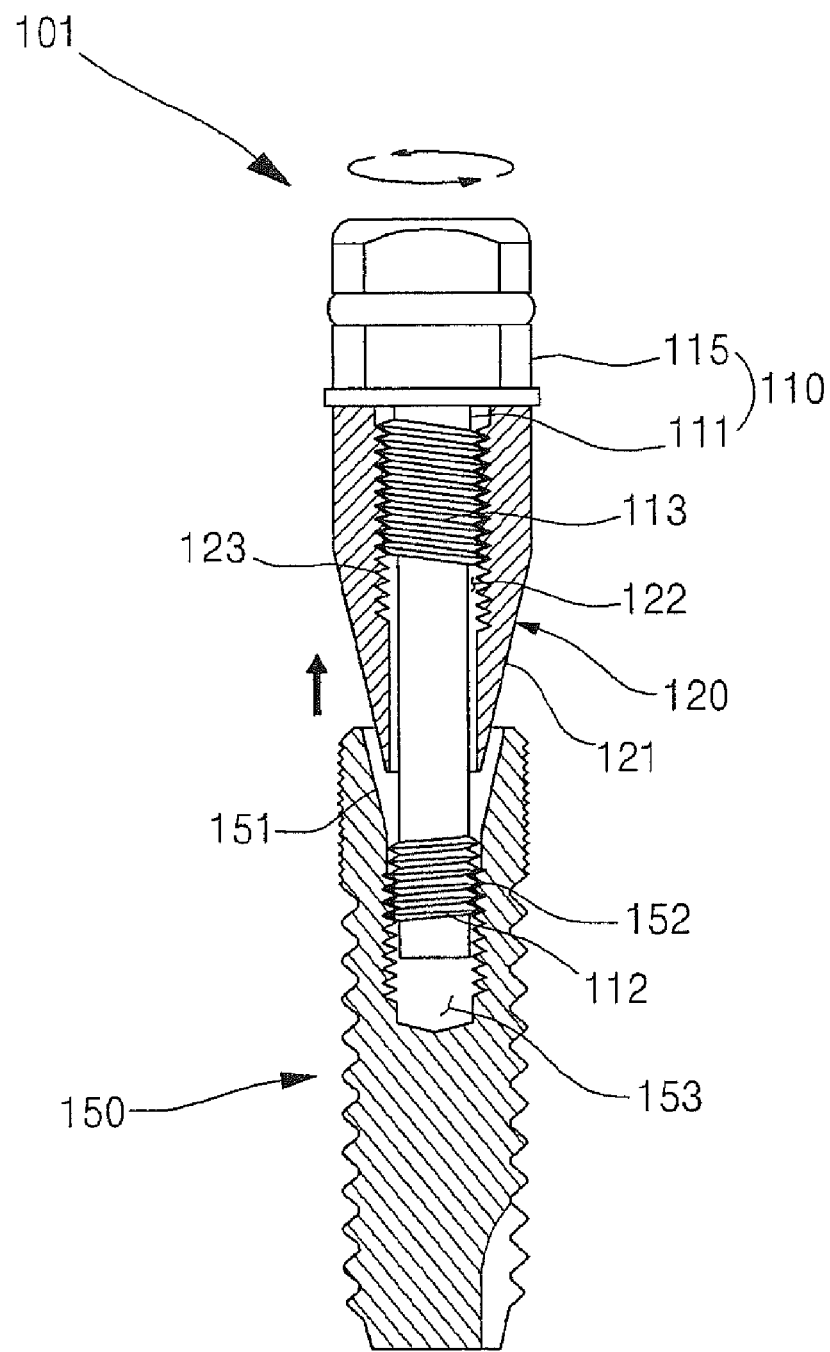
FIG. 5 is a view illustrating a state in which a head portion of the mount contacts an upper end portion of the mount in the mount device for a dental implant of FIG. 4.
Figure 6:
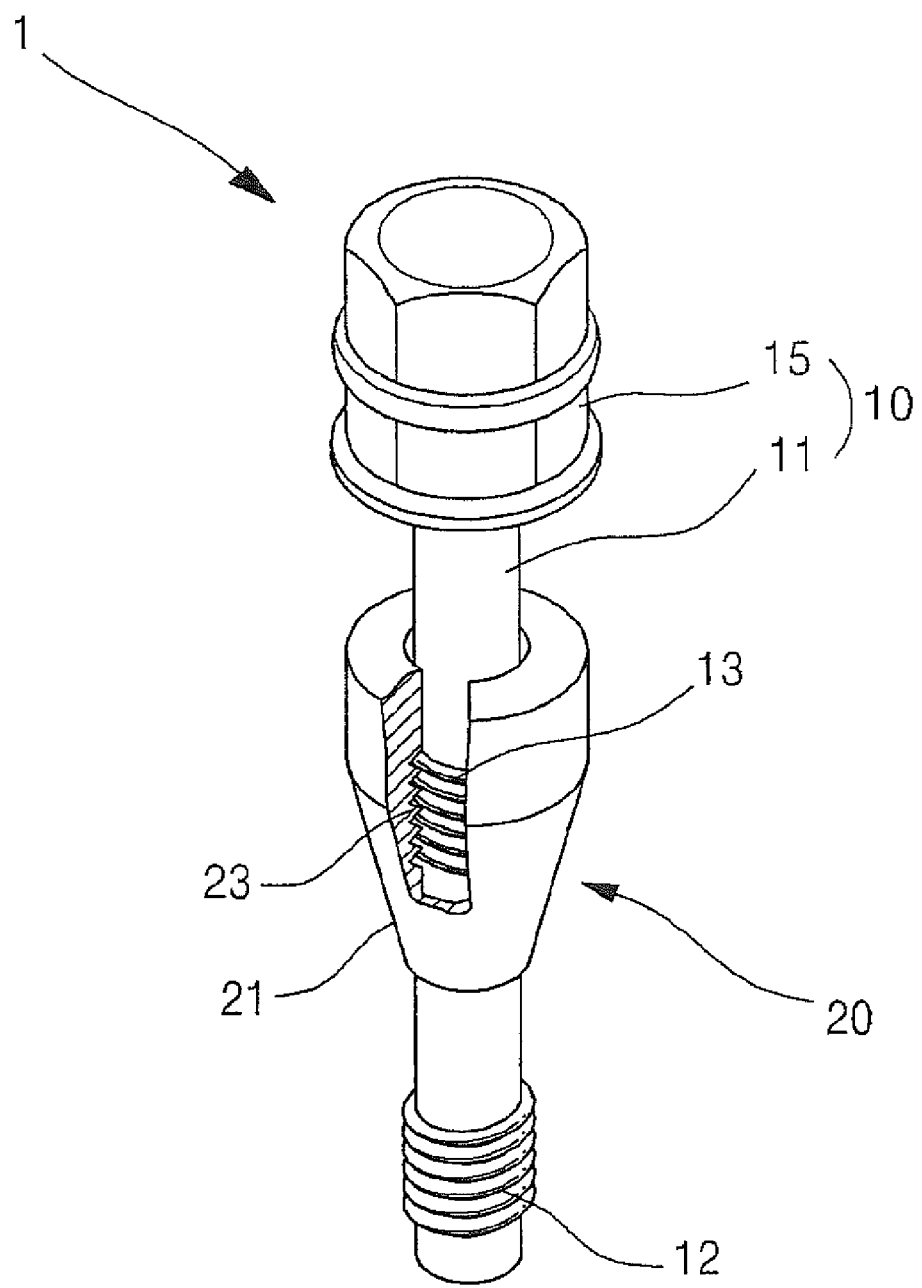
FIG. 6 is an exploded perspective view of a mount device for a dental implant according to an embodiment of the present invention.

The attached drawings for illustrating preferred embodiments of the present invention are referred to in order to gain a sufficient understanding of the present invention, the merits thereof, and the objectives accomplished by the implementation of the present invention.

Hereinafter, the present invention will be described in detail by explaining preferred embodiments of the invention with reference to the attached drawings. Like reference numerals in the drawings denote like elements.

Referring to FIGS. 6 through 9, a mount device 1 for a dental implant according to an embodiment of the present invention is generally used when a fixture 50 is placed in an alveolar bone. The fixture 50 includes an inner hole 53 inwardly formed to a predetermined depth along the lengthwise direction from the upper end to the lower end and a first inner screw portion 52 formed on an inner wall of the inner hole 53. The mount device 1 includes a mount screw 10 and a mount 20 screw coupled to the mount screw 10.

The mount screw 10 includes a body portion 11 and a head portion 15 having a sectional area larger than that of the body portion 11 and coupled to an upper end portion of the body portion 11. The body portion 11 includes a first screw portion 12 provided at a lower end portion thereof to be capable of screw coupling with a first inner screw portion 52 of the fixture 50 and a second screw portion 13 provided at the body portion 11 at a position separated a predetermined distance upward from the first screw portion 12 and having a screw formed in a direction opposite to a direction of a screw of the first screw portion 12. When the fixture 50 is placed, a dental handpiece (not shown) is detachably coupled to the head portion 15 through a handpiece connector (not shown).

The mount 20 includes an inclined surface 21 formed on an outer wall of the lower end portion for a conical connection to the upper end portion of the fixture 50, an insertion hole 22 formed along the lengthwise direction of the mount 20 from the upper end thereof to the lower end by penetrating the same, and a second inner screw portion 23 formed on the inner wall of the insertion hole 22. Also, to remove the screw coupling between the second inner screw portion 23 of the mount 20 and the second screw portion 13 of the mount screw 10 when the upper end portion of the mount 20 contacts the lower end surface of the head portion 15 of the mount screw 10, the distance $L_2$ from the lower end of the second inner screw portion 23 of the mount 20 to the upper end of the mount 20 is set to be less than the distance $L_1$ from the upper end of the second screw portion 13 of the mount screw 10 to the lower end of the head portion 15.

The mount screw 10 includes the body portion 11 and the head portion 15 as described above. The first screw portion 12 of the body portion 11 is a right screw while the second screw portion 13 is a left screw. The right screw proceeds forward into a female screw when rotated in the same direction as a direction to rotated a male screw clockwise, that is, a screw proceeding forward by being rotated to the right. The left screw is a screw which proceeds forward by being rotated to the left. When the fixture 50 is placed in an alveolar bone, the first screw portion 12 of the body portion 11 is screw coupled to the first inner screw portion 52 of the fixture 50 and the second screw portion 13 of the body portion 11 is screw coupled to the second inner screw portion 23 of the mount 20. When the mount screw 10 is rotated and placed in the alveolar bone, the mount 20 is moved toward the fixture 50 so that the mount 20 and the fixture 50 are coupled to each other to contact each other. The head portion 15 is detachably coupled to the handpiece (not shown) through a handpiece connector (not shown) and has a hexagonal head. The handpiece is capable of rotating forward and backward, that is, clockwise or counterclockwise.

The mount 20 has a shape such that the outer diameter of a lower end portion thereof decreases toward the lower end. Accordingly, the outer wall of the mount 20 forms the inclined surface 21. The inclined surface 21 has a conical connection to a fixture inner inclined surface 51 formed on the inner wall of the fixture 50 when the mount screw 10 is rotated and placed in the alveolar bone.

When the fixture 50 is placed as above, by coupling the second inner screw portion 23 of the mount 20 to the second screw portion 13 of the mount screw 10, and the first inner screw portion 52 of the fixture 50 to the first screw portion 12 of the mount screw 10, and rotating the mount screw 10 using the handpiece, the mount screw 10 is rotated, not relatively, but together with the fixture 50.

Figure 7:
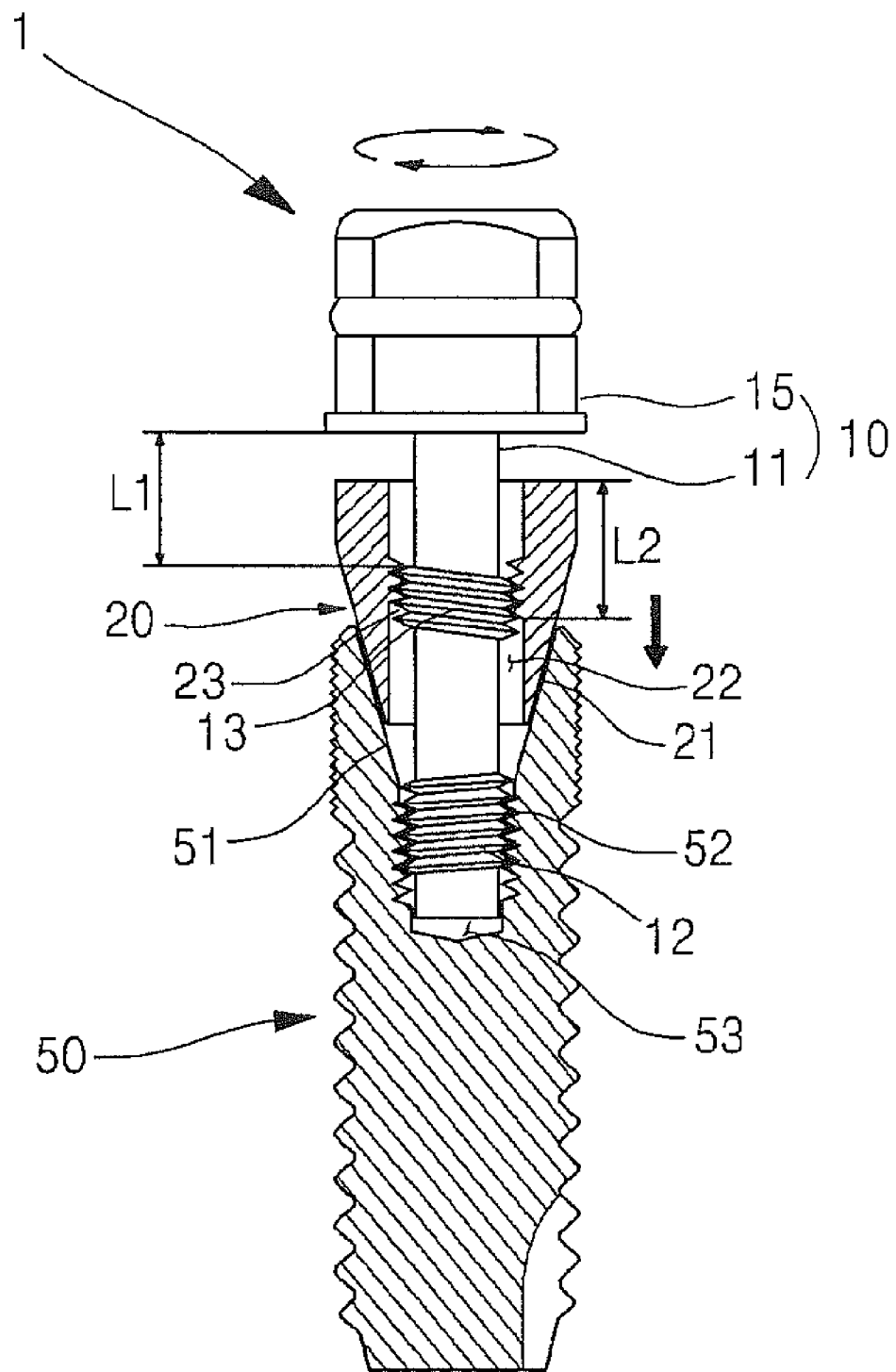
FIG. 7 is a sectional view illustrating a state in which the fixture is placed using the mount device for a dental implant of FIG. 6.

This is because, in addition to the screw coupling between the first screw portion 12 of the mount screw 10 and the first inner screw portion 52 of the fixture 50, the mount 20 is moved in a direction in which the second screw portion 13 of the mount screw 10, which is a left screw, and the second inner screw portion 23 of the mount 20 are separated from each other when the mount screw 10 is rotated clockwise by the handpiece. Thus, as shown in FIG. 7, as the inclined surface 21 of the mount 20 and the fixture inner inclined surface 51 closely contact each other, a frictional force is applied therebetween so that the fixture 50 is rotated together with the mount screw 10. That is, since, in addition to the screw coupling between the first screw portion 12 of the mount screw 10 and the first inner screw portion 52 of the fixture 50, the frictional force between the inclined surface 21 of the mount 20 and the fixture inner inclined surface 51, where a contact area is large, acts as a main force to rotate the fixture 50.

Figure 8:
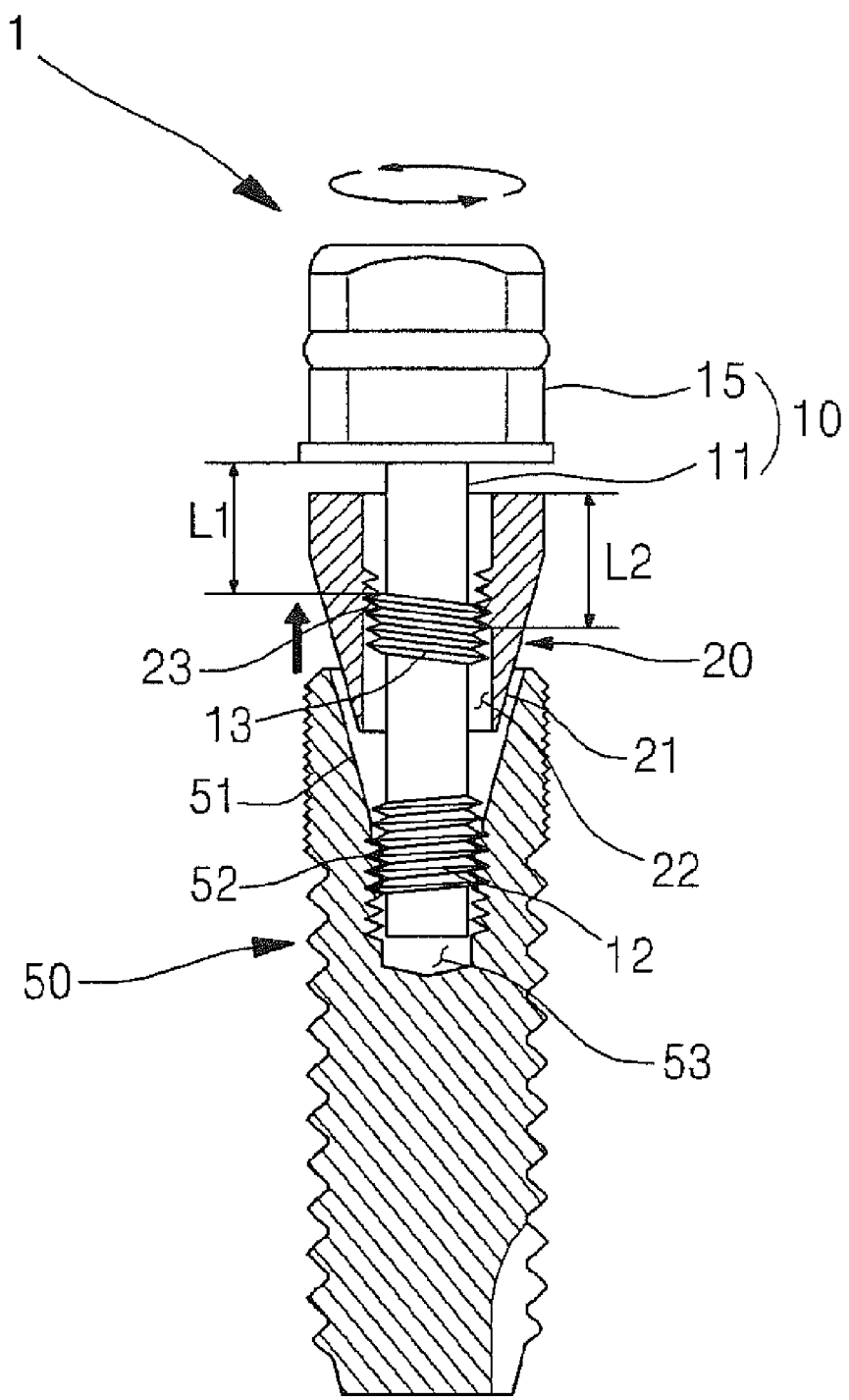
FIG. 8 is a sectional view illustrating a state in which the mount device for a dental implant of FIG. 7 is separated after the fixture is placed.

Reversely, to remove the mount device 1 after the fixture 50 is placed, the mount holder (not shown) is coupled to the mount 20 and the mount screw 10 is rotated counterclockwise that is reverse to the direction for placement using the handpiece while fixing the mount 20 using the mount holder or rotating the mount 20 clockwise using the mount holder. Then, the mount 20 moves upward as shown in FIG. 8 in a direction to screw couple the second inner screw portion 23 of the mount 20 and the second screw portion 13 of the mount screw 10. As a result, the state in which the inclined surface 21 of the mount 20 and the fixture inner inclined surface 51 are pressed against each other is removed and the frictional force does no longer act between the inclined surface 21 of the mount 20 and the fixture inner inclined surface 51. Therefore, only the mount screw 10 is relatively rotated with respect to the fixture 50 placed in the alveolar bone so as to be separated from the fixture 50.

In the present invention, in order to remove the screw coupling between the second inner screw portion 23 of the mount 20 and the second screw portion 13 of the mount screw 10 when or before the upper end surface of the mount 20 contacts the lower end surface of the head portion 15, the handpiece can rotate counterclockwise even when the mount holder continuously fixes the mount 20. Thus, to make the mount screw connected to the handpiece continuously rotate counterclockwise, the distance $L_2$ from the lower end of the second inner screw portion 23 of the mount 20 to the upper end of the mount 20 is set to be less than the distance $L_1$ from the upper end of the second screw portion 13 of the mount screw 10 to the lower end of the head portion 15.

Figure 9:
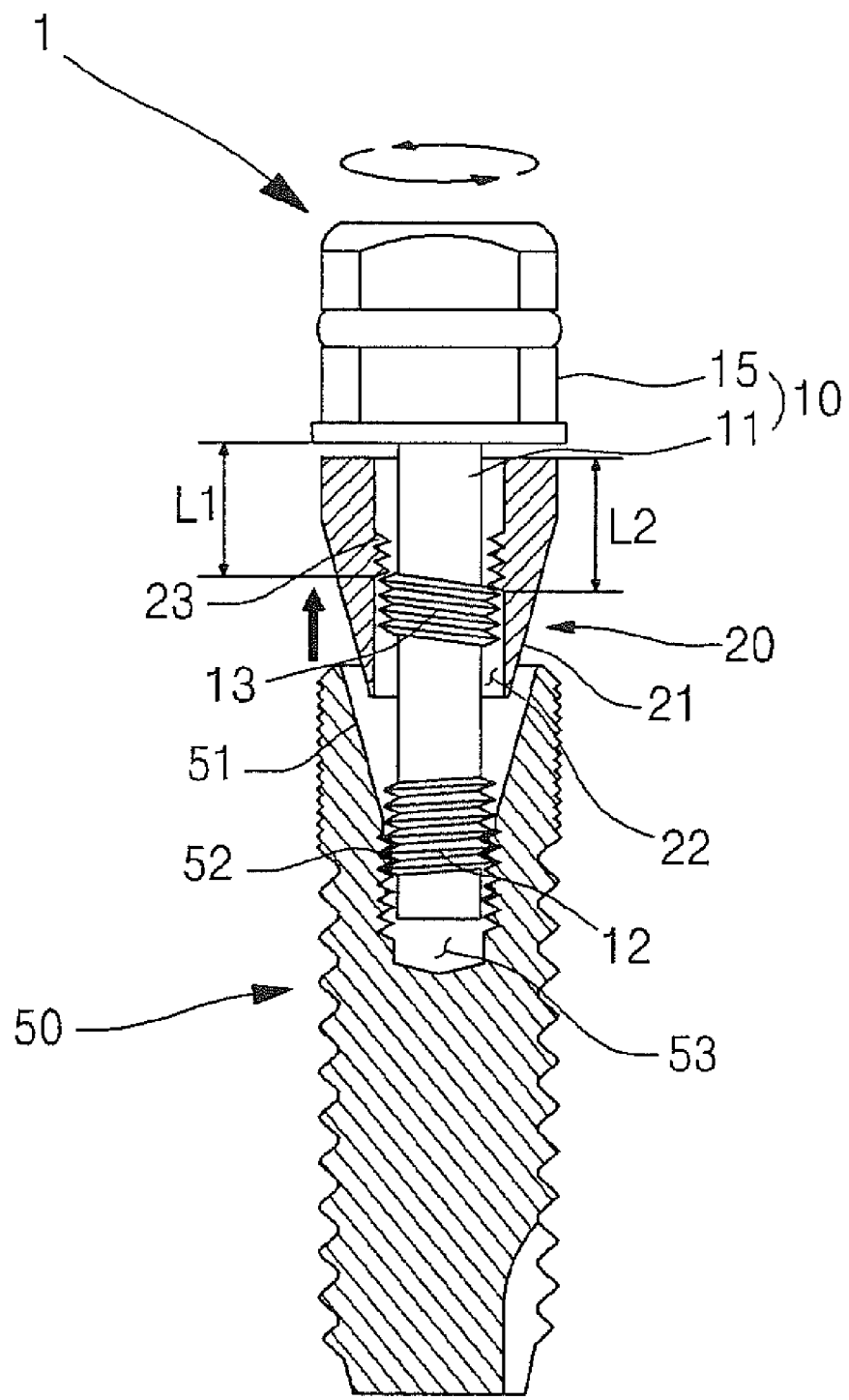
FIG. 9 is a sectional view illustrating a state in which the screw coupling between the second inner screw portion of the mount and the second screw portion of the mount screw is removed in the mount device for a dental implant of FIG. 7.

According to the above structure, even when the mount 20 moves upward toward the mount screw 10 by the rotation of the mount screw 10, since the screw coupling between the second inner screw portion 23 of the mount 20 and the second screw portion 13 of the mount screw 10 is removed when or before the upper end surface of the mount 20 contacts the lower end surface of the head portion 15, as shown in FIG. 9, the handpiece and the mount screw 10 connected thereto can be continuously rotated counterclockwise while the mount holder is fixed to the mount 20, so that the mount device 1 can be separated from the fixture 50. Therefore, compared to the conventional technology, an implant operation is made very easy and the operation time is reduced so that the pain of patients undergoing operations is alleviated and convenience is provide to dentists. In particular, when a slugging ring wrench is used as the mount holder, such effects can be maximized.

In the present embodiment, the distance $L_2$ from the lower end of the second inner screw portion 23 of the mount 20 to the upper end of the mount 20 is set to be 0.01-3 mm shorter than the distance $L_1$ from the upper end of the second screw portion 13 of the mount screw 10 to the lower end of the head portion 15.

According to the above-described structure, when the fixture 50 is placed in the alveolar bone using the mount device 1 for a dental implant according the above embodiment, the second inner screw portion 23 of the mount 20 is screw coupled to the second screw portion 13 of the mount screw 10 and the mount screw 10 is inserted in the inner hole 53 of the fixture 50 so that the first inner screw portion 52 of the fixture 50 and the first screw portion 12 of the mount screw 10 are screw coupled to each other.

Next, the handpiece is coupled to the head portion 15 of the mount screw 10 through the hand piece connector and the handpiece is rotated clockwise. Then, a force is generated which moves the mount 20 downward in a direction in which the screw coupling between the second inner screw portion 23 of the mount 20 and the second screw portion 13 of the mount screw 10 is removed according to the rotation of the mount screw 10. Accordingly, the inclined surface 21 of the mount 20 and the fixture inner inclined surface 51 closely contact each other and a frictional force acts therebetween. With the frictional force as a main force, the fixture 50 is rotated together with the mount screw 10 and thus placed in the alveolar bone.

To remove the mount device 1 after the replacement is completed, by fixing the mount holder to the mount 20 and rotating the mount screw 10 in the reverse direction, the mount 10 moved upward in a direction for screw coupling according to the rotation of the mount screw 10. Accordingly, the frictional force between the inclined surface 21 of the mount 20 and the fixture inner inclined surface 51 is removed. Also, since the screw coupling between the second inner screw portion 23 of the mount 20 and the second screw portion 13 of the mount screw 10 is removed when or before the upper end surface of the mount 20 contacts the lower end surface of the head portion 15, the state in which the mount screw 10 cannot be rotated further does not occur unlike the conventional technology. Thus, the mount device 1 can be separated from the fixture 50 without disassembling the mount holder from the mount 20.

Thereafter, the fixture 50 is osseointegrated to be completely fixed to the alveolar bone like a root of a natural tooth. After the osseointegration, an abutment (not shown) is connected to the fixture 50 and an artificial crown is mounted thereon, so that an implant artificial tooth is completed.

Hereinafter, a mount device for a dental implant according to another embodiment of the present invention will be described in detail with reference to the accompanying drawings. However, descriptions on the same elements in the above-described elements in the mount device for a dental implant according to the above-described embodiment will be omitted herein.

Figure 10:
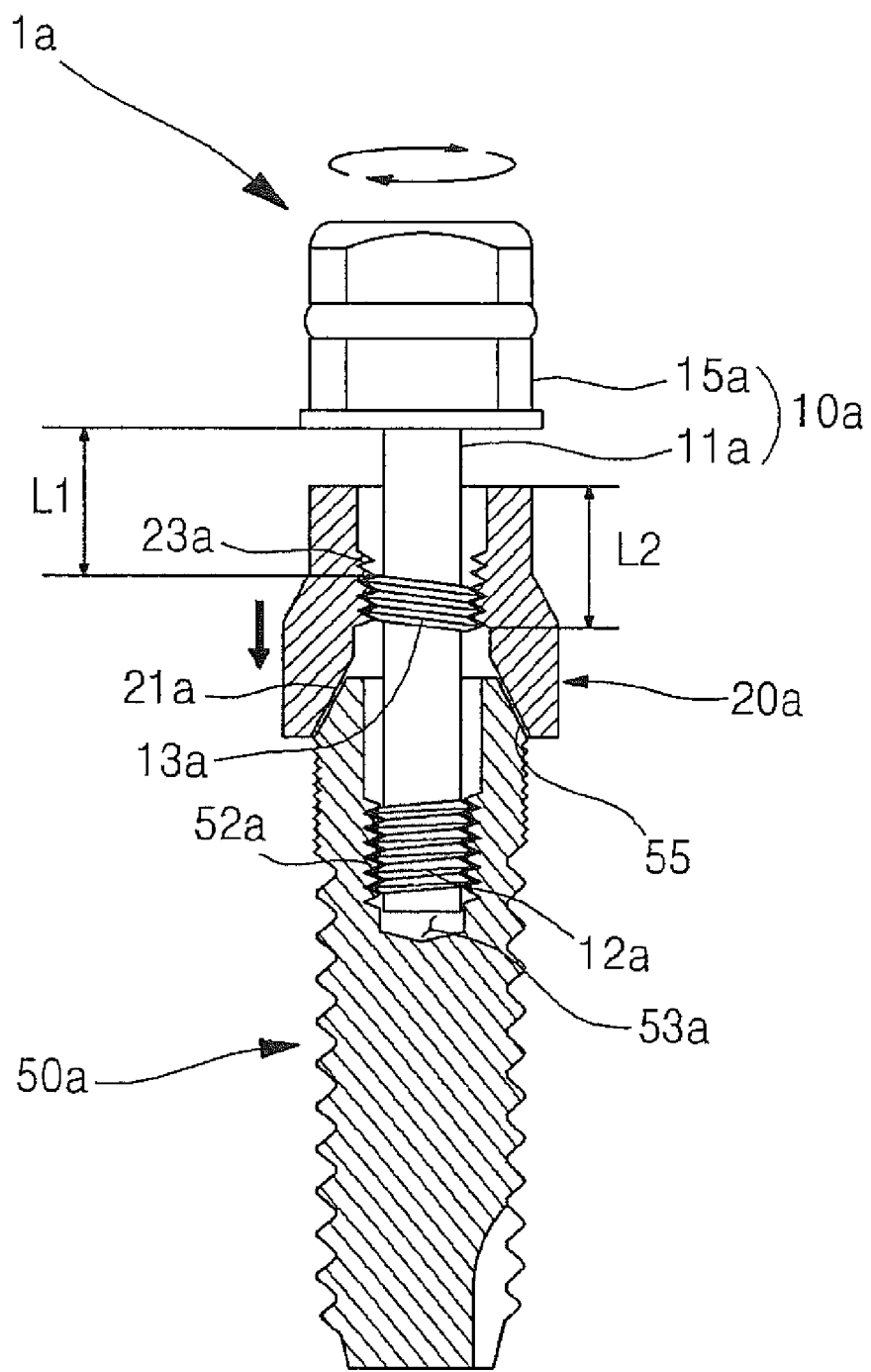
FIG. 10 is a sectional view illustrating a state in which the fixture is placed using a mount device for a dental implant according to another embodiment of the present invention.
Figure 11:
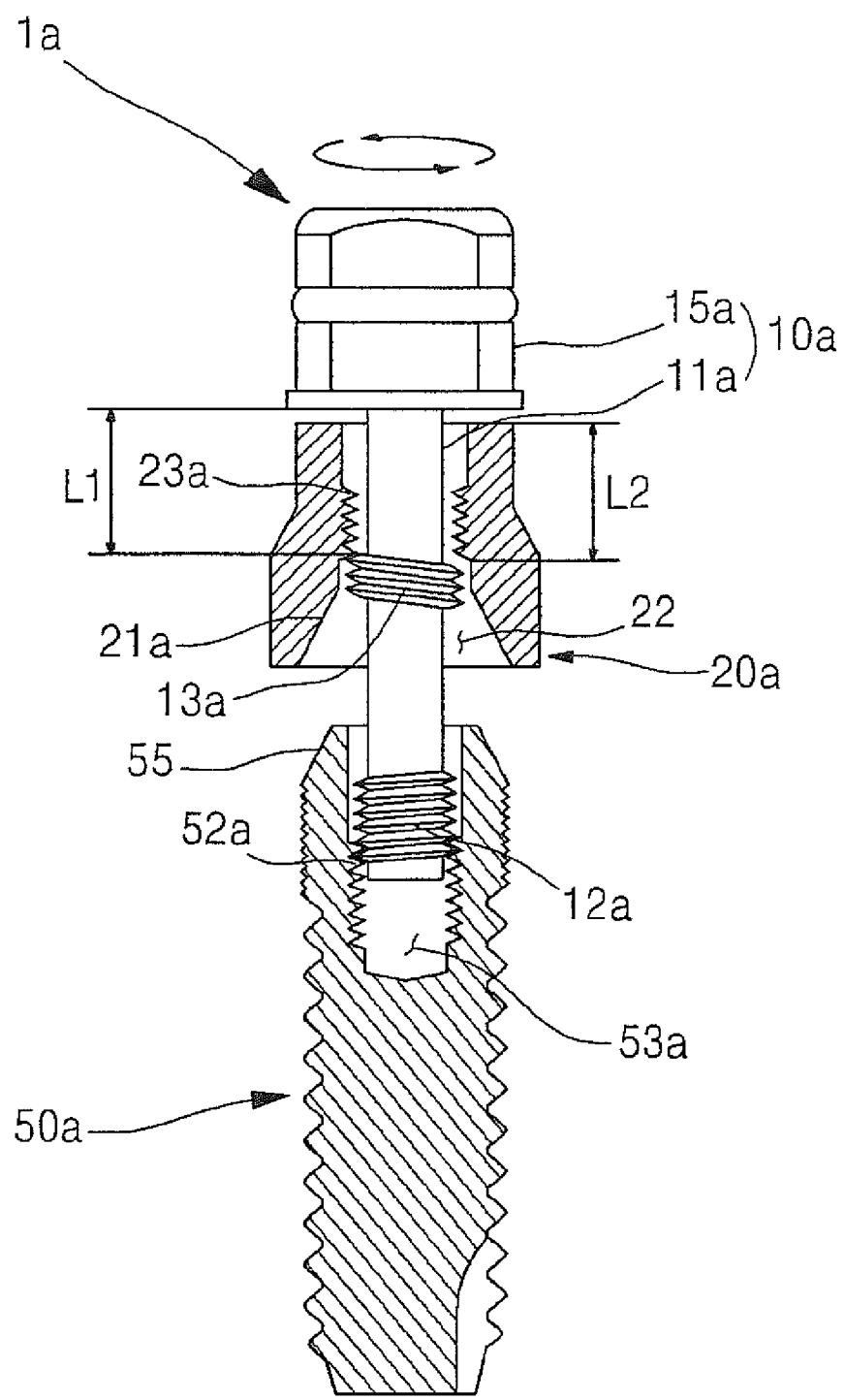
FIG. 11 is a sectional view illustrating a state in which the screw coupling between the second inner screw portion of the mount and the second screw portion of the mount screw is removed in the mount device for a dental implant of FIG. 10.

FIG. 10 is a sectional view illustrating a state in which the fixture is placed using a mount device for a dental implant according to another embodiment of the present invention. FIG. 11 is a sectional view illustrating a state in which the screw coupling between the second inner screw portion of the mount and the second screw portion of the mount screw is removed in the mount device for a dental implant of FIG. 10.

As shown in FIGS. 10 and 11, in a mount device 1a for a dental implant according to another embodiment of the present invention, a lower end portion of a mount 20a has an inner diameter that increases toward the lower end such that an inclined surface 21a of the mount 20a is formed on an inner wall of the lower end portion of the mount 20a. It is the only difference from the previous embodiment that the inclined surface 21a has a conical connection to a fixture outer inclined surface 55 formed on an outer wall of the fixture 50a. In the present embodiment, since the inclined surface 21a of the mount 20a is formed inside the mount 20a and the fixture outer inclined surface 55 contacts the inclined surface 21a of the mount 20a, a possibility of the upper end portion of the fixture 50a being damaged is remarkably reduced compared to the conventional technology.

In the above-described embodiments, the first screw portion of the mount screw is a right screw while the second screw portion is a left screw. However, in a special case, it is possible that the first screw portion of the mount screw is a left screw while the second screw portion is a right screw.

While this invention has been particularly shown and described with reference to preferred embodiments thereof, it will be understood by those skilled in the art that various changes in form and details may be made therein without departing from the spirit and scope of the invention as defined by the appended claims.

As described above, according to the present invention, the mount device for a dental implant has a simple structure and can remove the mount device without disassembling the mount holder from the mount so that an implant operation is made very easy and the operation time can be greatly reduced, compared to the conventional technology, while solving the inconvenience in the operation according to the conventional technology in which the mount device can be removed by stopping the rotation of the handpiece at a certain time point and removing the mount holder from the mount and then continuously rotating the handpiece counterclockwise while rotating the handpiece connected to the mount screw through the handpiece connector counterclockwise with the mount holder fixed to the mount to remove the mount device after the fixture is placed in the alveolar bone.

Accordingly, the implant operation is made easy and the operation time is greatly reduced, compared to the conventional technology, so that the pain of patients undergoing operations is alleviated and convenience is provided to dentists, thus increasing the possibility of success of an operation.

Furthermore, since the lower end portion of the mount has an inner diameter that increases toward the lower end thereof such that the inclined surface of the mount is formed on the inner wall of the lower end portion of the mount, and the inclined surface of the mount has a conical connection to the outer inclined surface of the fixture formed on the outer wall of the fixture, the possibility of the upper end portion of the fixture being damaged is further reduced compared to the conventional technology.

What is claimed is:

1. A mount device for a dental implant to place a fixture in an alveolar bone, the fixture having an inner hole formed inside to have a predetermined depth along a lengthwise direction from an upper end of the fixture to a lower end thereof, the mount device comprising:

a mount screw including a body portion having a first screw portion provided at the lower end of the body portion to be capable of screw coupling to a first inner screw portion of the fixture and a second screw portion having a screw formed in a direction opposite to a direction of a screw of the first screw portion and provided at a position separated a predetermined distance upward from the first screw portion, and a head portion having a sectional area larger than that of the body portion, coupled to an upper end portion of the body portion, and detachably coupled to a handpiece for a dental use through a handpiece connector; and a mount having an inclined surface formed on at least one of an inner wall and an outer wall of the lower end portion for a conical connection to the upper end portion of the fixture, an insertion hole formed inside the mount along a lengthwise direction from the upper end to a lower end thereof by penetrating the mount, and a second inner screw portion formed on an inner wall of the insertion hole and capable of screw coupling to the second screw portion, wherein, to remove a screw coupling between the second inner screw portion of the mount and the second screw portion of the mount screw when an upper end surface of the mount contacts a lower end surface of the head portion of the mount screw, a distance from a lower distal end of the second inner screw portion of the mount to the upper proximal end of the mount is less than a distance from an upper proximal end of the second screw portion of the mount screw to a lower distal end of the head portion.

2. The mount device of claim 1, wherein a lower end portion of the mount has an outer diameter which decreases toward a lower end thereof so that the inclined surface is formed on an outer wall of the lower end portion of the mount, and the inclined surface has a conical connection to a fixture inner inclined surface formed on the inner wall of the fixture.

3. The mount device of claim 1, wherein the first screw portion is a right screw and the second screw portion is a left screw.

4. The mount device of claim 1, wherein a distance from the lower distal end of the second inner screw portion of the mount to the upper proximal end of the mount is 0.01-3 mm shorter than a distance from the upper proximal end of the second screw portion of the mount screw to the lower distal end of the head portion.

5. The mount device of claim 2, wherein a distance from a lower end of the second inner screw portion of the mount to the upper end of the mount is 0.01-3 mm shorter than a distance from an upper end of the second screw portion of the mount screw to a lower end of the head portion.

6. The mount device of claim 3, wherein a distance from a lower end of the second inner screw portion of the mount to the upper end of the mount is 0.01-3 mm shorter than a distance from an upper end of the second screw portion of the mount screw to a lower end of the head portion.

\* \* \* \* \*